US010980497B2

(12) United States Patent
Ohi (10) Patent No.: US 10,980,497 B2
(45) Date of Patent: Apr. 20, 2021

(54) NEEDLE BIOPSY APPARATUS, NEEDLE BIOPSY METHOD, AND NEEDLE BIOPSY SYSTEM

(71) Applicant: Shimadzu Corporation, Kyoto (JP)

(72) Inventor: Junichi Ohi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 308 days.

(21) Appl. No.: 16/040,710

(22) Filed: Jul. 20, 2018

(65) Prior Publication Data

US 2019/0029616 A1 Jan. 31, 2019

(30) Foreign Application Priority Data

Jul. 26, 2017 (JP) .............................. JP2017-144164

(51) Int. Cl.
*A61B 6/00* (2006.01)
*A61B 6/12* (2006.01)
*A61B 10/02* (2006.01)
*A61B 6/03* (2006.01)
*A61B 90/00* (2016.01)

(52) U.S. Cl.
CPC ............... *A61B 6/12* (2013.01); *A61B 6/037* (2013.01); *A61B 6/4057* (2013.01); *A61B 6/481* (2013.01); *A61B 10/0233* (2013.01); *A61B 2090/392* (2016.02); *A61B 2090/3966* (2016.02)

(58) Field of Classification Search
None
See application file for complete search history.

(56) References Cited

U.S. PATENT DOCUMENTS

| 5,647,374 | A | 7/1997 | Cutrer |
| 6,175,760 | B1 * | 1/2001 | Baskin ................ A61B 6/4258 600/431 |
| 8,082,023 | B2 | 12/2011 | Yarnall |
| 2013/0345550 | A1 | 12/2013 | Rafaeli et al. |

FOREIGN PATENT DOCUMENTS

| CN | 106388872 A | 2/2017 |
| JP | 5249754 B2 | 12/2008 |

OTHER PUBLICATIONS

Japanese Office Action dated Sep. 29, 2020, in connection with corresponding JP Application No. 2017-144164 (7 pp., including machine-generated English translation).
Chinese Office Action dated Dec. 3, 2020, in connection with corresponding CN Application No. 201810812396.8 (15 pp., including machine-generated English translation).

* cited by examiner

*Primary Examiner* — Joel F Brutus
(74) *Attorney, Agent, or Firm* — Maier & Maier, PLLC

(57) ABSTRACT

A needle biopsy apparatus includes: a hollow needle for needling a patient; and a main body portion which retains the needle, and acquires a tissue of the patient through the needle. The needle is configured of gas not including a radioactive label, a liquid not including a radioactive label, or a solid not including a radioactive label, and includes a labelling portion of which a radiation dose to be detected is less than that of the tissue of the patient ingesting a radioactive-labelled radiopharmaceutical dosed to the patient, on a tip end side.

9 Claims, 9 Drawing Sheets

FIG.1
FIRST EMBODIMENT

FIG.2A
FIRST EMBODIMENT

SIDE VIEW

FIG.2B
FIRST EMBODIMENT

SECTIONAL VIEW ALONG LINE 200-200

FIG.4

FIRST EMBODIMENT

FIG.5

FIRST EMBODIMENT

FIG.6A
FIRST EMBODIMENT

PERFORM NEEDLING OF NEEDLE

FIG.6B
FIRST EMBODIMENT

REACH LESION AREA

FIG.6C
FIRST EMBODIMENT

START TISSUE ACQUISITION

FIG.6D
FIRST EMBODIMENT

ACQUIRE TISSUE

FIG.7
SECOND EMBODIMENT

FIG.8A
THIRD EMBODIMENT
SIDE VIEW

FIG.8B
THIRD EMBODIMENT
SECTIONAL VIEW ALONG LINE 300-300

FIG.10A
FIRST MODIFICATION EXAMPLE OF FIRST EMBODIMENT
SIDE VIEW

FIG.10B
FIRST MODIFICATION EXAMPLE OF FIRST EMBODIMENT

SECTIONAL VIEW ALONG LINE 400-400

FIG.11
FIRST MODIFICATION EXAMPLE OF FIRST EMBODIMENT

FIG.12

SECOND MODIFICATION EXAMPLE OF FIRST EMBODIMENT

FIG.13

MODIFICATION EXAMPLE OF SECOND EMBODIMENT

NEEDLE BIOPSY APPARATUS, NEEDLE BIOPSY METHOD, AND NEEDLE BIOPSY SYSTEM

CROSS-REFERENCE OF RELATED APPLICATIONS

The priority application number JP2017-144164, NEEDLE BIOPSY APPARATUS, NEEDLE BIOPSY METHOD, AND NEEDLE BIOPSY SYSTEM, filed on Jul. 26, 2017, Junichi Ohi, upon which this patent application is based are hereby incorporated by reference.

FIELD

The present invention relates to a needle biopsy apparatus, a needle biopsy method, and a needle biopsy system, and in particular, relates to a needle biopsy apparatus, a needle biopsy method, and a needle biopsy system, performing an examination using a nuclear medical diagnostic equipment.

BACKGROUND

In the related art, a needle biopsy system provided with a needle biopsy apparatus performing an examination by using a nuclear medical diagnostic equipment is known. Such needle biopsy apparatus, needle biopsy method, and needle biopsy system, for example, are disclosed in the specification of U.S. Pat. No. 5,647,374 and Japanese Patent No. 5249754.

The nuclear medical diagnostic equipment is a equipment which detects a radiation emitted from a radioactive isotope (RI) dosed to a patient, and images the radiation. In particular, in cancer diagnosis, a radiopharmaceutical in which a glucose analog is RI-labelled, is dosed to the patient, and a radiation emitted from the RI-labelled radiopharmaceutical accumulated in the cancer is detected, on the basis of the characteristics that a glycometabolism of a cancer is brisker than that of the other cell, and thus, the location, the size, or the like of the cancer is confirmed. In addition, a needle biopsy is an examination of acquiring a tissue in the body through a needle which is needled to a lesion area of the patient from the outside, in order to perform a pathological examination or the like with respect to the tissue in the body. Specifically, the needle biopsy is used at the time of acquiring a tumor tissue, in order to confirm whether a tumor is malignant or benign. However, in general, the needle used in the needle biopsy does not include an RI radiation source (a radiation source) emitting a radiation, and thus, is difficult to be confirmed in an image generated by the nuclear medical diagnostic equipment.

Therefore, in the needle biopsy apparatus disclosed in the specification of U.S. Pat. No. 5,647,374 and Japanese Patent No. 5249754, the RI radiation source (the radiation source) is disposed on a needle tip in order to be detected by the nuclear medical diagnostic equipment, and is used as a marker. That is, the RI radiation source is disposed on the needle tip, and thus, a radiation is emitted from the RI radiation source. The radiation emitted from the RI radiation source on the needle tip is detected by a detector of the nuclear medical diagnostic equipment, and thus, the position of the needle tip is confirmed in the image.

However, the needle biopsy apparatus disclosed in the specification of U.S. Pat. No. 5,647,374 and Japanese Patent No. 5249754, includes the radiation source on a tip end side of the needle. Therefore, it is necessary to sufficiently manage the radiation source disposed on the biopsy needle, and thus, the handling of the needle biopsy apparatus becomes cumbersome. In addition, a radiation dosage of the patient and an operator increases due to the RI radiation source disposed on the biopsy needle. Furthermore, herein, the "operator" indicates a doctor, an engineer, a nurse, or the like performing the needle biopsy.

The invention has been made in order to solve the problems described above, and one object of the invention is to provide a needle biopsy apparatus, a needle biopsy method, and a needle biopsy system, in which it is possible to make management and handling of a biopsy needle under a nuclear medical diagnostic equipment easy, and to reduce a dosage of a patient and an operator.

SUMMARY

In order to attain the object described above, the present inventors have conducted intensive studies, and thus, have found that in a nuclear medical diagnostic equipment, in a case where a radiation dose detected by a detector is small, in an image to be obtained, a portion of which the radiation dose is small, is drawn in whiter (as a low-count region) than the other portion. On the basis of such findings, a needle biopsy apparatus according to a first aspect of the invention, for performing a needle biopsy with respect to a patient while imaging at least a part of a needle, by using a nuclear medical diagnostic equipment, includes: a hollow needle for needling the patient; and a main body portion which retains the needle, and acquires a tissue of the patient through the needle, in which the needle is configured of gas not including a radioactive label, a liquid not including a radioactive label, or a solid not including a radioactive label, and includes a labelling portion of which a radiation dose to be detected by a detection unit of the nuclear medical diagnostic equipment is less than that of the tissue of the patient ingesting a radioactive-labelled radiopharmaceutical dosed to the patient, on a tip end side. Furthermore, herein, the "radioactive label" indicates that a part of an element contained in a substance is substituted with a radioactive isotope element. In addition, "not including a radioactive label" indicates that the radioactive label is not substantially included, and allows the radioactive label to be included to the extent that the radiation is not detected by the detection unit of the nuclear medical diagnostic equipment.

As described above, the needle biopsy apparatus according to the first aspect of the invention includes the hollow needle for needling the patient, and the main body portion which retains the needle, and acquires the tissue of the patient through the needle, in which the needle is configured of the gas not including the radioactive label, the liquid not including the radioactive label, or the solid not including the radioactive label, and includes the labelling portion of which the radiation dose to be detected by the detection unit of the nuclear medical diagnostic equipment is less than that of the tissue of the patient ingesting the radioactive-labelled radiopharmaceutical dosed to the patient, on the tip end side. Here, in the nuclear medical diagnostic equipment, in a case where the radiation dose detected by the detector is small, a portion in which the radiation dose is small, is drawn as a low-count (outline) region in an image to be obtained, compared to the other normal tissue or a cancer tissue. Therefore, the labelling portion of which the radiation dose to be detected by the detection unit of the nuclear medical diagnostic equipment is small, is included on the tip end side of the needle, and thus, it is possible to confirm the position of the biopsy needle as the low-count (the outline) region in the image, without disposing a radioactive-labelled labelling portion in the needle. As a result thereof, it is possible to perform the needle biopsy by the needle not including the radioactive-labelled labelling portion (an RI radiation source), and thus, it is possible to make the management and the handling of the biopsy needle under the nuclear medical diagnostic equipment easy, and to reduce the dosage of the patient and the operator.

In the needle biopsy apparatus according to the first aspect described above, it is preferable that the labelling portion includes an air or liquid radiation absorber, or a solid radiation absorber. Here, in a case where the labelling portion contains air, the labelling portion does not include an RI radiation source, and thus, a radiation dose emitted from the labelling portion is less than a radiation dose emitted from the other portion, and therefore, it is possible to decrease the radiation dose to be detected by the detector. In addition, in a case where the radiation absorber is provided in the labelling portion, a radiation emitted from the body of the patient is absorbed by the radiation absorber, and thus, it is possible to further decrease the radiation dose to be detected by the detector, than the air. Therefore, in a case where the labelling portion includes the air or liquid radiation absorber, or the solid radiation absorber, it is possible to reduce the radiation dose to be detected by the detector, and to confirm the tip end side (the labelling portion) of the needle in the image.

In the needle biopsy apparatus according to the first aspect described above, it is preferable that the labelling portion includes a radiation absorber which absorbs a radiation emitted from the radioactive-labelled radiopharmaceutical dosed to the patient, more than a structure portion of the needle other than the labelling portion. According to such a configuration, it is possible to further increase an absorption amount of the radiation in the labelling portion of the biopsy needle, than the structure portion of the needle other than the labelling portion. As a result thereof, it is possible to easily identify the tip end side (the labelling portion) of the biopsy needle in the image to be acquired by the nuclear medical diagnostic equipment.

In the needle biopsy apparatus according to the first aspect described above, it is preferable that the radiation absorber is disposed separately from the needle, and is formed in the needle into the shape of a cylinder along an inner circumferential surface of the needle. According to such a configuration, the radiation absorber is formed into the shape of a cylinder, and thus, it is possible to allow the tissue to penetrate through the radiation absorber at the time of acquiring the tissue. As a result thereof, it is possible to perform the needle biopsy in a state where the biopsy needle is disposed on the tissue to be acquired, without retreating the radiation absorber from the needle at the time of acquiring the tissue, and thus, it is possible to shorten a procedure time.

In the needle biopsy apparatus according to the first aspect described above, it is preferable that in the needle, at least the tip end side is formed of the radiation absorber. According to such a configuration, it is possible to integrally dispose the labelling portion as a part of the needle. As a result thereof, it is possible to confirm the needle in the image to be acquired by the nuclear medical diagnostic equipment, without disposing the radiation absorber separate from needle in the needle, and thus, it is possible to suppress an increase in the number of components of the needle biopsy apparatus.

In the needle biopsy apparatus according to the first aspect described above, it is preferable that the radiation absorber is disposed separately from the needle, and is disposed in the needle to be detachable. According to such a configuration, the tissue is acquired after the radiation absorber is retreated from the needle, and thus, it is possible to increase a freedom degree of selecting the shape, the material, or the like of the radiation absorber disposed in the needle.

In the needle biopsy apparatus according to the first aspect described above, it is preferable that the liquid or the solid of the labelling portion is a radiation absorber having specific gravity of greater than or equal to 1 g/ml. According to such a configuration, in the labelling portion, it is possible to reduce the radiation dose to be detected by the detector.

A needle biopsy method according to a second aspect of the invention, includes: a step of needling a needle of a needle biopsy apparatus provided with a hollow needle, which is configured of gas not including a radioactive label, a liquid not including a radioactive label, or a solid not including a radioactive label, and includes a labelling portion of which a radiation dose to be detected by a detection unit of a nuclear medical diagnostic equipment is less than that of a tissue of a patient ingesting a radioactive-labelled radiopharmaceutical dosed to the patient, towards a lesion area of the patient; a step of capturing an image of a region including the labelling portion and the lesion area to which the radioactive-labelled radiopharmaceutical is dosed, by using the nuclear medical diagnostic equipment; and a step of acquiring the tissue from the lesion area by the needle, on the basis of a position of the labelling portion and the lesion area in the image.

As described above, the needle biopsy method according to the second aspect of the invention includes the step of needling the needle of the needle biopsy apparatus provided with the hollow needle, which is configured of the gas not including the radioactive label, the liquid not including the radioactive label, or the solid not including the radioactive label, and includes the labelling portion of which the radiation dose to be detected by the detection unit of the nuclear medical diagnostic equipment is less than that of the tissue of the patient ingesting the radioactive-labelled radiopharmaceutical dosed to the patient, towards the lesion area of the patient, the step of capturing the image of the region including the labelling portion and the lesion area to which the radioactive-labelled radiopharmaceutical is dosed, and the step of acquiring the tissue from the lesion area by the needle. Accordingly, even in a case where the needle biopsy is performed by the biopsy needle not using the RI radiation source as the labelling portion, it is possible to confirm the position tip end side of the needle by the labelling portion, and to perform the needling towards the lesion area. As a result thereof, it is possible to perform the needle biopsy by the needle not including the radioactive-labelled labelling portion, and thus, it is possible to make the management and the handling of the biopsy needle under the nuclear medical diagnostic equipment easy, and to reduce the dosage of the patient and the operator.

A needle biopsy system according to a third aspect of the invention, includes: a needle biopsy apparatus; and a nuclear medical diagnostic equipment, in which the needle biopsy apparatus for performing a needle biopsy with respect to a patient while imaging at least a part of a needle, by using the nuclear medical diagnostic equipment includes a hollow needle for needling the patient, and, and a main body portion which retains the needle, and acquires a tissue of the patient through the needle, the needle is configured of gas not including a radioactive label, a liquid not including a radioactive label, or a solid not including a radioactive label, and includes a labelling portion of which a radiation dose to be detected by a detection unit of the nuclear medical diagnostic equipment is less than that of the tissue of the patient ingesting a radioactive-labelled radiopharmaceutical dosed to the patient, on a tip end side, and the nuclear medical diagnostic equipment acquires an image of a region including the labelling portion and a lesion area of the patient.

As described above, the needle biopsy system according to the third aspect of the invention includes the needle biopsy apparatus, and the nuclear medical diagnostic equipment, in which the needle biopsy apparatus for performing the needle biopsy with respect to the patient while imaging at least a part of the needle, by using the nuclear medical diagnostic equipment, includes the hollow needle for needling the patient, and the main body portion which retains the needle, and acquires the tissue of the patient through the needle, the needle is configured of the gas not including the radioactive label, the liquid not including the radioactive label, or the solid not including the radioactive label, and includes the labelling portion of which the radiation dose to be detected by the detection unit of the nuclear medical diagnostic equipment is less than that of the tissue of the patient ingesting the radioactive-labelled radiopharmaceutical dosed to the patient, on the tip end side, and the nuclear medical diagnostic equipment acquires the image of the region including the labelling portion and the lesion area of the patient. Accordingly, even in a case where the needle biopsy is performed by the biopsy needle not using the RI radiation source as the labelling portion, it is possible to perform the needle biopsy while confirming the position of the tip end side of the biopsy needle by the image which is generated by the nuclear medical diagnostic equipment. As a result thereof, it is possible to perform the needle biopsy by the needle not including the radioactive-labelled labelling portion, and thus, it is possible to make the management and the handling of the biopsy needle under the nuclear medical diagnostic equipment easy, and to reduce the dosage of the patient and the operator.

DETAILED DESCRIPTION

Hereinafter, embodiments embodying the invention will be described on the basis of the drawings.

First Embodiment

A configuration of a needle biopsy system 100 including a needle biopsy apparatus 10 according to a first embodiment of the invention will be described, with reference to FIG. 1 to FIG. 6D.

(Configuration of Needle Biopsy System)

Figure 1:
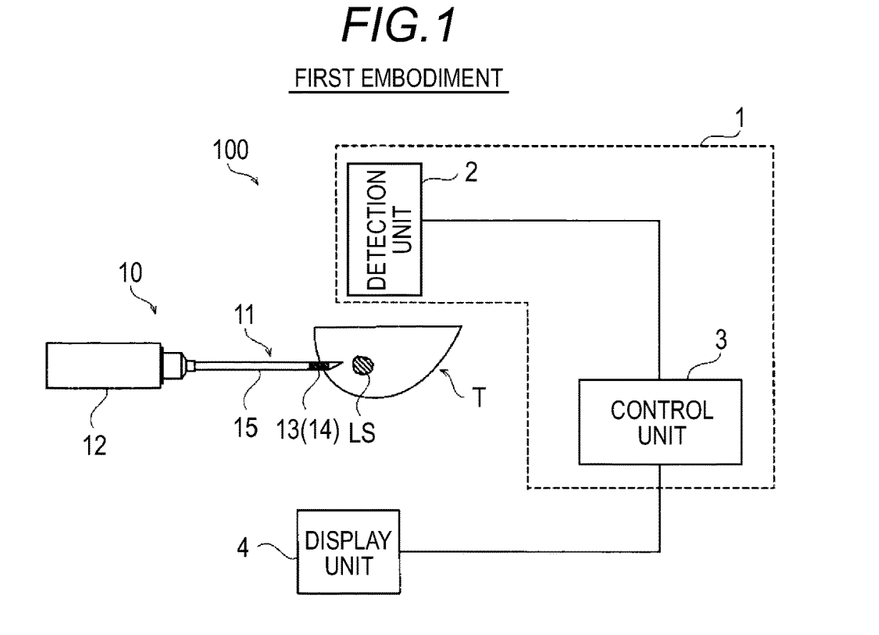
FIG. 1 is a diagram illustrating an overall configuration of a needle biopsy system according to a first embodiment.

As illustrated in FIG. 1, the needle biopsy system 100 includes the needle biopsy apparatus 10, a nuclear medical diagnostic equipment 1, and a display unit 4. The needle biopsy apparatus 10 is a device acquiring a lesion area LS of a patient T through a needle 11. The detailed configuration of the needle biopsy apparatus 10 will be described below.

The nuclear medical diagnostic equipment 1 is a device which detects a radiation emitted from a radioactive isotope (RI)—labelled radiopharmaceutical (not illustrated) dosed to the patient T, and images a distribution of radiation sources in the patient T. The nuclear medical diagnostic equipment 1, for example, is used for a diagnosis of a cancer, or the like. In the first embodiment, the nuclear medical diagnostic equipment 1 is used for a diagnosis of a breast cancer of the patient T. Furthermore, in FIG. 1, for convenience, only a breast portion of the patient T is illustrated.

The nuclear medical diagnostic equipment 1, for example, includes a positron emission tomography device (PET) in which a plurality of detection units 2 are arranged into the shape of a ring, a gamma camera detecting a γ radiation source, a single-photon emission computed tomography (SPECT), and the like. Furthermore, a positron emission mammography device (PEM) specifying a positron-emitting source, in which a plurality of detection units 2 are arranged into the shape of a pair of plates, a breast specific positron emission tomography device in which a plurality of detection units 2 are arranged around the breast into the shape of a ring, and the like are used for an examination of a breast cancer.

In addition, a radioactive-labelled (RI-labelled) radiopharmaceutical, for example, distinguishes a cancer cell from a usual cell on the basis of the characteristics that glycometabolism of the cancer cell is brisker than that of the usual cell at the time of diagnosing a cancer, and thus, 18F-FDG (fluorodeoxyglucose) is used as a radiopharmaceutical. 18F-FDG indicates that a hydroxyl group on a 2-position of glucose is substituted with 18F. 18F-FDG is a glucose analog, and thus, is ingested by a cell, but the hydroxyl group on the 2-position is substituted with 18F, and thus, is accumulated in the cell without being metabolized by the cell. The nuclear medical diagnostic equipment 1 detects a radiation emitted from 18F-FDG accumulated in the cell, and thus, is capable of imaging the distribution of the radiation source in the body of the patient T.

As illustrated in FIG. 1, the nuclear medical diagnostic equipment 1 includes a detection unit 2 and a control unit 3. For example, in of the positron emission tomography device, the detection unit 2 is configured by arranging a plurality of detector modules including a light receiving sensor (not illustrated) such as a photomultiplier tube or a silicon photomultiplier (SiPM), and a plurality of scintillators (not illustrated) arranged in predetermined two directions on the light receiving sensor at a predetermined cycle (a pixel pitch) into the shape of an array, into the shape of a ring. The detection unit 2 detects the radiation emitted from the RI-labelled radiopharmaceutical dosed to the patient T, converts the detected radiation into an electric signal, and reads the converted electric signal as an image signal. In addition, the detection unit 2 outputs the acquired image signal to the control unit 3.

The control unit 3 generates a nuclear medical diagnosis image 5 (refer to FIG. 3A), on the basis of the image signal output from the detection unit 2. The control unit 3, for example, includes a central processing unit (CPU), a graphics processing unit (GPU), and the like.

Furthermore, in the first embodiment, the nuclear medical diagnostic equipment 1 is connected to the display unit 4. The control unit 3 outputs the generated image to the display unit 4.

The display unit 4 displays the nuclear medical diagnosis image 5 (refer to FIG. 3A) output from the control unit 3. The display unit 4 includes a monitor such as a liquid crystal display.

(Configuration of Needle Biopsy Apparatus)

Next, the configuration of the needle biopsy apparatus 10 will be described, with reference to FIGS. 2A and 2B. The needle biopsy apparatus 10 is a needle biopsy apparatus for performing a needle biopsy with respect to the patient T while imaging at least a part of the needle 11, by using the nuclear medical diagnostic equipment 1.

Figure 2A:
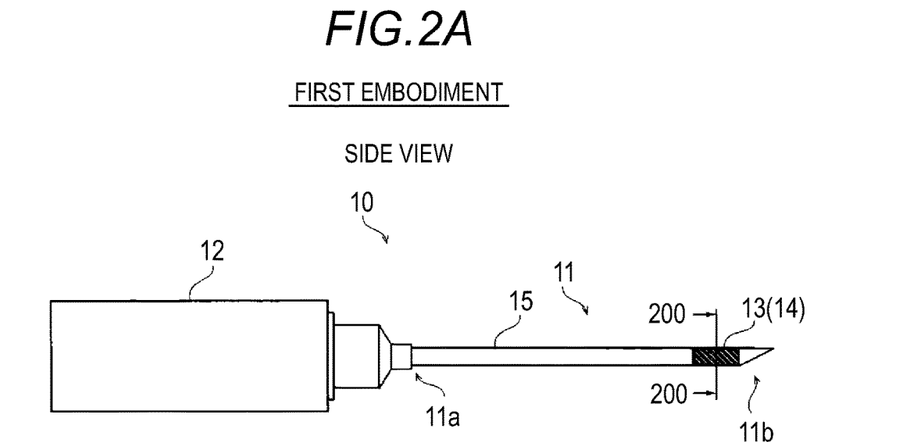
FIG. 2A is a schematic view when a needle biopsy apparatus according to the first embodiment is seen from a side surface.

As illustrated in FIG. 2A, in the first embodiment, the needle biopsy apparatus 10 includes a hollow needle 11 for needling the patient T, and a main body portion 12 which retains the needle 11, and acquires a tissue O of a lesion area LS (refer to FIG. 6C) of the patient T through the needle 11.

The needle 11 is configured of a solid not including a radioactive label. For example, the needle 11 is configured of a metal. The metal used in the needle 11, for example, includes stainless steel, titanium, or the like. The needle 11 is formed into the shape of a cylinder, and includes a proximal end 11a close to the main body portion 12 and a distal end 11b separated from the main body portion 12.

As illustrated in FIG. 2A, the distal end 11b of the needle 11 is needled to the patient T, and thus, is formed to have a sharp shape. In addition, the needle 11 has a height and an inner diameter at which the tissue O can be acquired from the lesion area LS of the patient T. The height of the needle 11, for example, is 75 mm to 200 mm. In addition, the inner diameter of the needle 11, for example, is 2 mm. Furthermore, the needle 11 may have any height and any inner diameter, insofar as the needle 11 is capable of acquiring the tissue O from the lesion area LS of the patient T.

In addition, the needle 11 includes a labelling portion 13 of which a radiation dose to be detected by the detection unit 2 of the nuclear medical diagnostic equipment 1 is less than that of the tissue O in the lesion area LS of the patient T ingesting a radioactive label (an RI label) dosed to the patient T, on a tip end side (the distal end 11b side). In the nuclear medical diagnosis image 5, the labelling portion 13 is disposed to allow an operator to recognize the position of the needle 11.

Figure 2B:
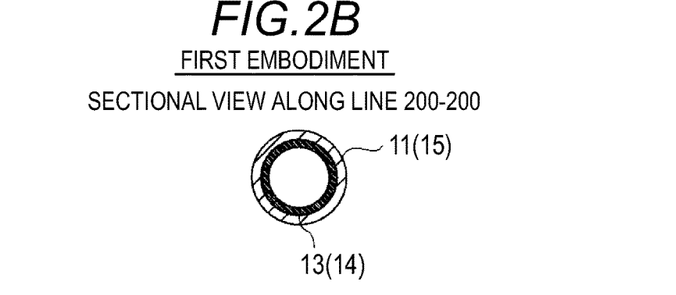
FIG. 2B is a sectional view along line 200-200 of FIG. 2A.

In addition, as illustrated in FIG. 2B, the labelling portion 13 is disposed separately from the needle 11, and is formed in the needle 11 into the shape of a cylinder along an inner circumference of the needle 11. In an example illustrated in FIG. 2B, the labelling portion 13 is formed into a shape across the entire inner circumference of the needle 11, but may not be formed across the entire inner circumference.

Figure 3A:
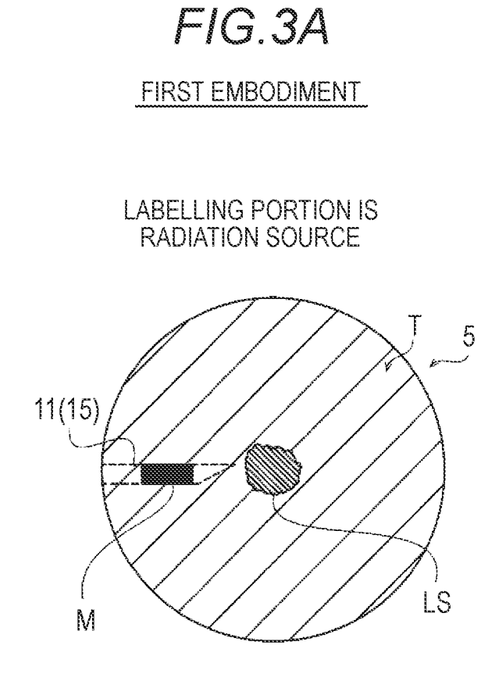
FIG. 3A is a schematic view of a nuclear medical diagnosis imagenuclear medical diagnosis image in a case where a labelling portion is a radiation source.
Figure 3B:
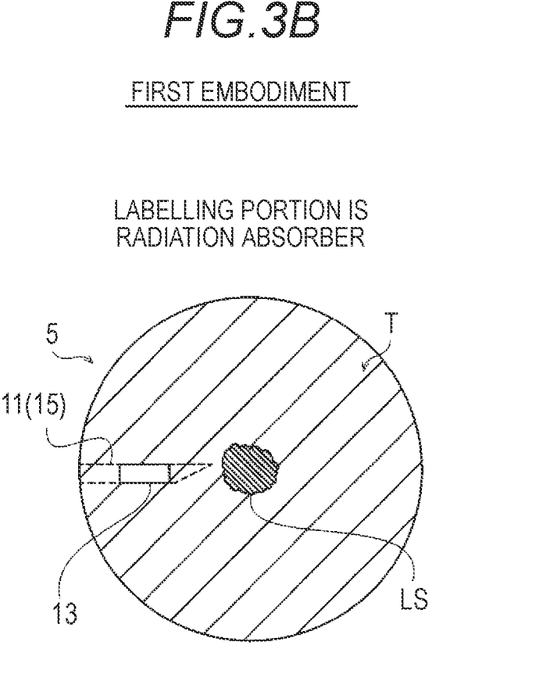
FIG. 3B is a schematic view of the nuclear medical diagnosis image in a case where the labelling portion is a radiation absorber.

Here, the labelling portion 13 of the first embodiment, and a known technology using a radiation source as the labelling portion 13 will be described, with reference to FIGS. 3A and 3B. FIG. 3A is a schematic view of the nuclear medical diagnosis image 5 imaged by using a marker M formed of a radiation source (an RI radiation source), and a range within a hatched line is a viewing field in which imaging can be performed. FIG. 3B is a schematic view of the nuclear medical diagnosis image 5 imaged by using the labelling portion 13. 18F-FDG used in the first embodiment is the glucose analog, and thus, is ingested not only in the cancer cell but also in the usual cell. Therefore, in the nuclear medical diagnosis image 5 illustrated in FIG. 3A and FIG. 3B, the background (the usual cell, the tissue, and the like) is approximately uniformly drawn with a pixel value reflecting an ingested amount of 18F-FDG with respect to the usual cell. In addition, the glycometabolism of the lesion area LS (the cancer cell) is brisker than that of the usual cell, and thus, in the lesion area LS, an accumulated amount of the radiopharmaceutical is large. Therefore, in the nuclear medical diagnosis image 5 illustrated in FIG. 3A and FIG. 3B, the lesion area LS is more densely represented, than the background (the usual cell, the tissue, and the like).

As illustrated in FIG. 3A, in a case of including the marker M formed of the radiation source (the RI radiation source), a radiation emitted from the marker M is detected by the detection unit 2, and thus, in the nuclear medical diagnosis image 5, the marker M is densely drawn. The radiation source used as the marker M is configured such that a radiation dose to be emitted is greater than that of the lesion area LS, in order to be easily confirmed in the nuclear medical diagnosis image 5.

As illustrated in FIG. 3B, in a case of the needle 11 including the labelling portion 13, the labelling portion 13 absorbs and/or scatters the radiation emitted from the body of the patient T, and thus, reduces the radiation dose to be detected by the detection unit 2. Here, in the nuclear medical diagnostic equipment 1, in a case where the radiation dose to be detected by the detection unit 2 is small, in the nuclear medical diagnosis image 5 to be obtained, a portion in which the radiation dose is small, is drawn in whiter (as a low-count region) than the other portion. Therefore, as illustrated in FIG. 3B, the labelling portion 13 of the first embodiment is drawn in white, in the nuclear medical diagnosis image 5. Furthermore, in the nuclear medical diagnosis image 5, the labelling portion 13 is drawn in whiter, as the absorption amount of the radiation increases. Therefore, in the nuclear medical diagnosis image 5, the lesion area LS, the background, and the labelling portion 13 are represented palely in this order.

From such a viewpoint, even under an environment where the entire background generates a certain amount of radiation due to dosed 18F-FDG, a region in which a radiation dose is relatively small (the labelling portion 13) is provided, and thus, as with the marker M illustrated in FIG. 3A, it is possible to recognize the labelling portion 13 by being distinguished from the other region. On the basis of such a viewpoint, the labelling portion 13 can be configured by disposing a region not ingesting 18F-FDG by a gas region of the air or the like, in the needle 11. In addition, the region becomes whiter as the radiation dose is relatively small, and thus, it is possible to obviously identify the region.

Therefore, as illustrated in FIG. 2A, in the first embodiment, the labelling portion 13 includes a radiation absorber 14. Specifically, the labelling portion 13 includes the radiation absorber 14 of which an absorption amount of the radiation emitted from the radioactive-labelled radiopharmaceutical dosed to the patient T is greater than that of a structure portion 15 of the needle 11 other than the labelling portion 13. Furthermore, in the first embodiment, the radiation absorber 14 is formed of a solid such as a metal.

In addition, in the first embodiment, the solid (the radiation absorber 14) of the labelling portion 13 includes the radiation absorber 14 of which specific gravity is greater than or equal to 1 g/ml. In addition, the absorption amount of the radiation increases as the specific gravity increases, and thus, it is preferable that the solid of the labelling portion 13 includes the radiation absorber 14 of which the specific gravity is greater than or equal to 8 g/ml, which is higher than that of stainless steel used in the needle 11. It is more preferable that the solid of the labelling portion 13 includes the radiation absorber 14 of which the specific gravity is greater than or equal to 10 g/ml. The solid (the radiation absorber 14) of the labelling portion 13, for example, contains a heavy metal such as lead, tungsten, and gold. It is preferable that tungsten, gold, or the like is used as the solid (the radiation absorber 14) of the labelling portion 13, since the specific gravity is approximately 20 g/ml, and thus, the absorption amount of the radiation is large, and tungsten, gold, or the like is drawn in whiter, in the nuclear medical diagnosis image 5. In addition, the size of the labelling portion 13 may be any size, insofar as being capable of being confirmed in the nuclear medical diagnosis image 5. It is preferable that the height of the labelling portion 13, for example, is greater than or equal to 2 mm.

The main body portion 12 is configured to acquire the tissue O from the lesion area LS of the patient T through the retained needle 11. In the first embodiment, the main body portion 12 is configured to sample the tissue O in the lesion area LS of the patient T with a force of a built-in spring (not illustrated), by manipulating a button (not illustrated).

(Method of Acquiring Tissue in Lesion Area of Patient)

Next, a method of acquiring the tissue O in the lesion area LS of the patient T by using the needle biopsy apparatus 10, under the nuclear medical diagnostic equipment 1, will be described, with reference to FIG. 4 to FIG. 6D.

Figure 4:
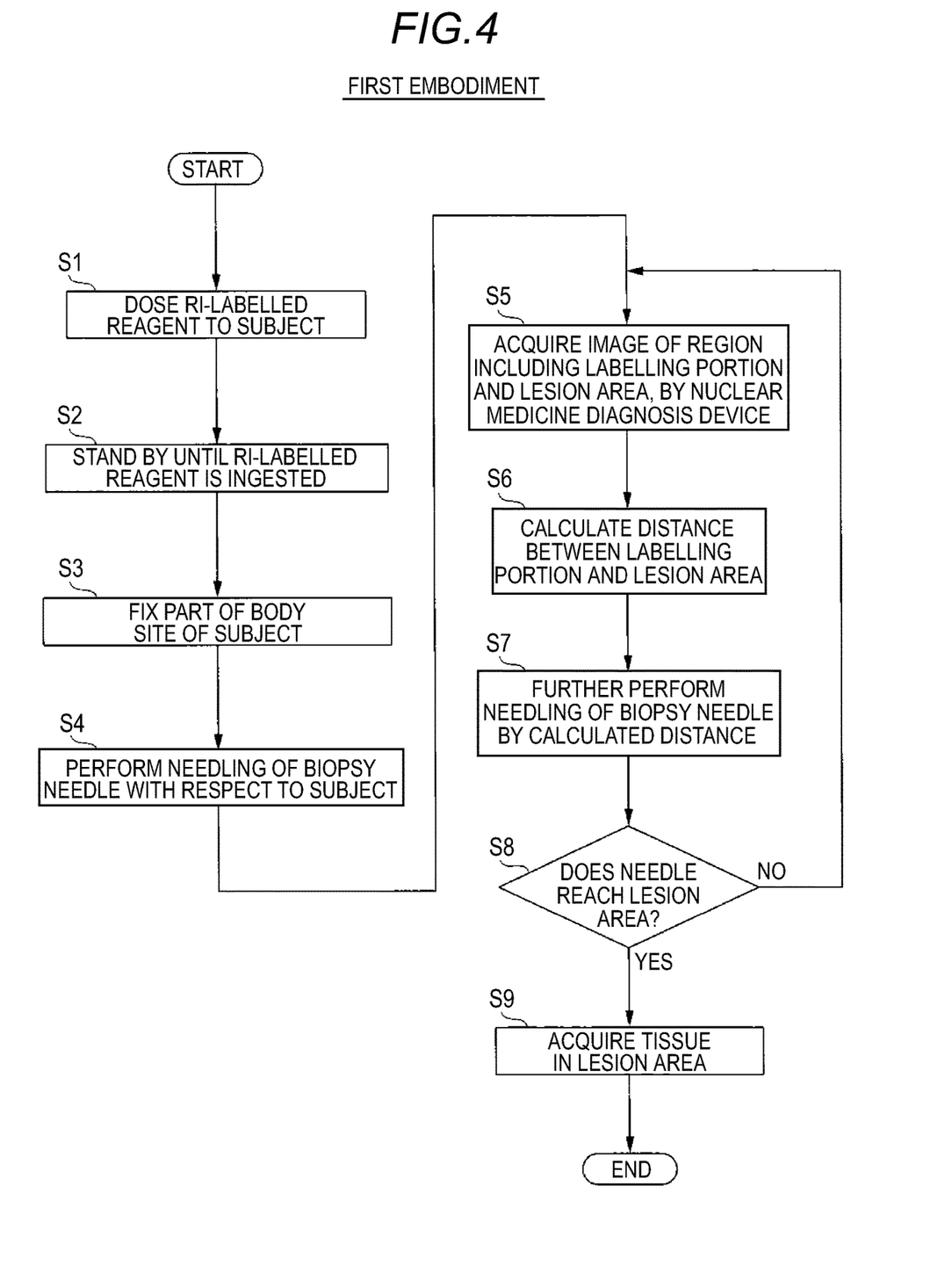
FIG. 4 is a flowchart for illustrating a needle biopsy method according to the first embodiment.

First, a flow of the method of acquiring the tissue O in the lesion area LS of the patient T will be described, with reference to FIG. 4.

In the first embodiment, the needle biopsy system 100 displays the image generated by the nuclear medical diagnostic equipment 1 on the display unit 4, and performs a needle biopsy while the operator confirms the displayed image.

In Step S1, the operator doses the radioactive-labelled (the RI-labelled) radiopharmaceutical to the patient T. Next, in Step S2, the operator stands by at rest for a predetermined time until the radioactive-labelled (RI-labelled) radiopharmaceutical dosed to the patient T is ingested to each of the tissues O. The predetermined time, for example, is approximately 1 hour, and then, there is a case where a laboratory examination is performed by a whole-body PET device. Next, the processing proceeds to Step S3.

Figure 5:
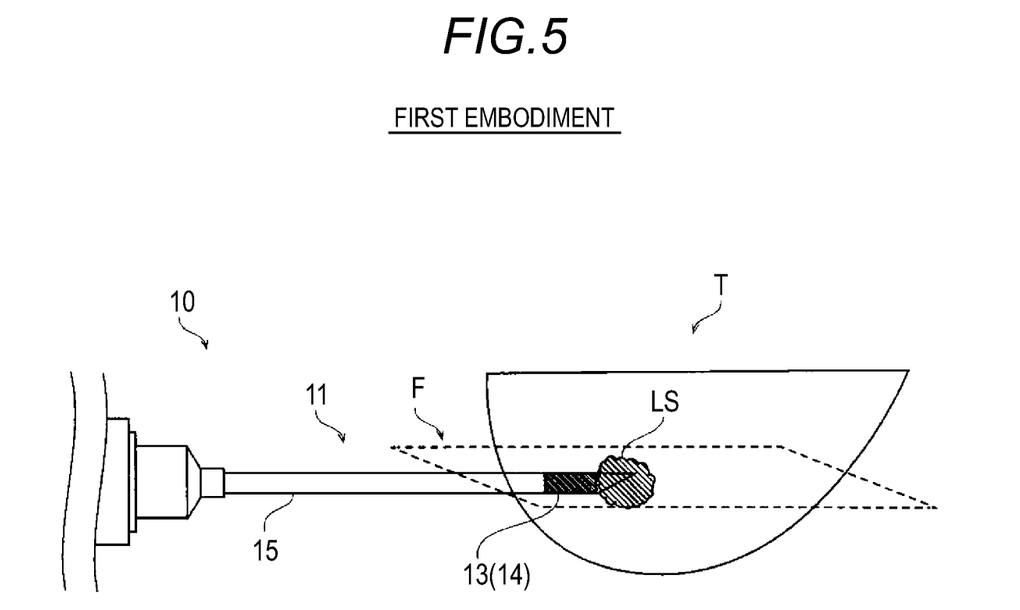
FIG. 5 is a schematic view for illustrating a method of acquiring a lesion area of a patient by the needle biopsy apparatus according to the first embodiment.

In Step S3, the operator fixes a part of a body site from which the tissue O of the patient T is acquired. That is, the body site including the lesion area LS of the patient T is fixed. After that, in Step S4, as illustrated in FIG. 5, the operator needles the biopsy needle 11 of the needle biopsy apparatus 10 towards the lesion area LS of the patient T. After that, the processing proceeds to Step S5.

FIGS. 6A to 6D are schematic views A to D of a tomographic image of a fault surface F in FIG. 5. The fault surface F is a fault surface including the labelling portion 13 of the needle 11. By including the labelling portion 13, it is possible to confirm the position of the labelling portion 13 in the nuclear medical diagnosis image 5 to be displayed on the display unit 4. Furthermore, for convenience, in FIGS. 6A to 6D, the structure portion 15 of the needle 11 other than the labelling portion 13 is illustrated by a broken line.

Figure 6A:
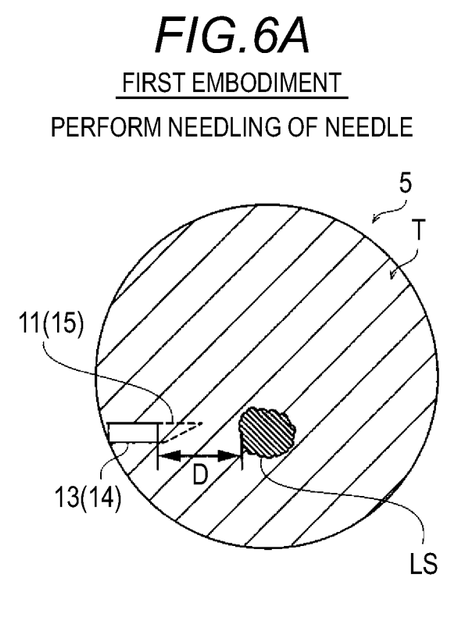
FIG. 6A is a schematic view of the nuclear medical diagnosis image when a biopsy needle is needled to the patient by the needle biopsy apparatus according to the first embodiment.

As illustrated in FIG. 6A, in Step S5, the operator acquires the nuclear medical diagnosis image 5 of a region including the lesion area LS and the labelling portion 13 by the nuclear medical diagnostic equipment 1. After that, in Step S6, the control unit 3 of the nuclear medical diagnostic equipment 1 calculates a distance D between the labelling portion 13 and the lesion area LS, from the acquired nuclear medical diagnosis image 5. After that, the processing proceeds to Step S7.

Figure 6B:
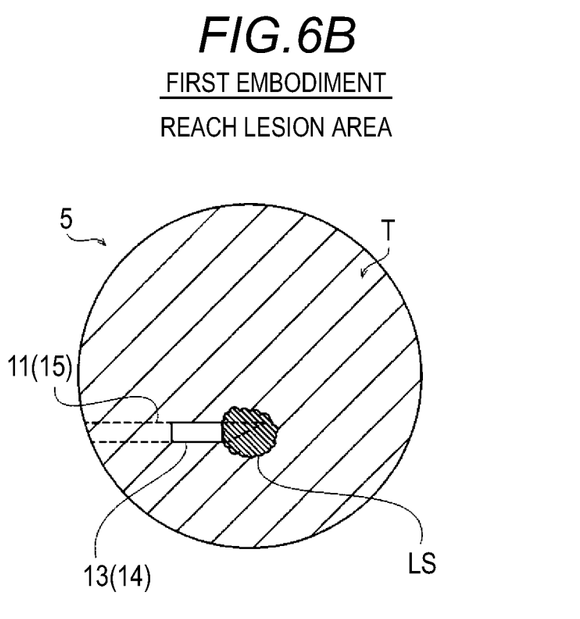
FIG. 6B is a schematic view of the nuclear medical diagnosis image when the biopsy needle of the needle biopsy apparatus according to the first embodiment reaches the lesion area of the patient.

In Step S7, the operator further needles the needle 11, by the distance D calculated in Step S6. After that, as illustrated in FIG. 6B, in Step S8, the operator acquires the nuclear medical diagnosis image 5 by the nuclear medical diagnostic equipment 1, and confirms whether or not the tip end (the labelling portion 13) of the needle 11 reaches the lesion area LS. In a case where the tip end (the labelling portion 13) of the needle 11 does not reach the lesion area LS, the processing returns to Step S5. In a case where the tip end (the labelling portion 13) of the needle 11 reaches the lesion area LS, the processing proceeds to Step S9.

Figure 6C:
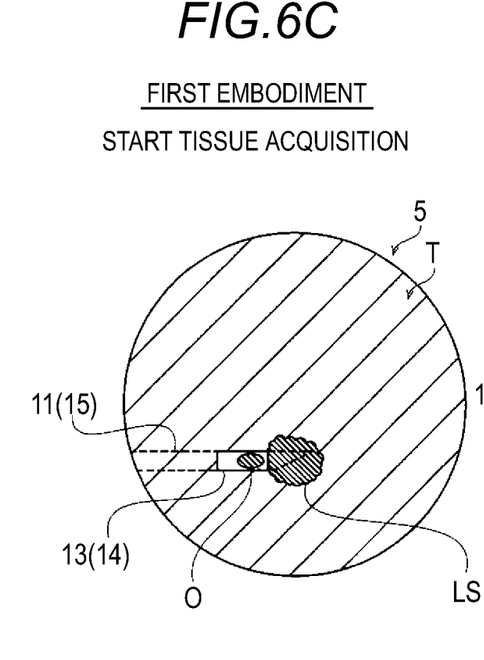
FIG. 6C is a schematic view of the nuclear medical diagnosis image when a tissue of the lesion area of the patient is started to be acquired by the needle biopsy apparatus according to the first embodiment.
Figure 6D:
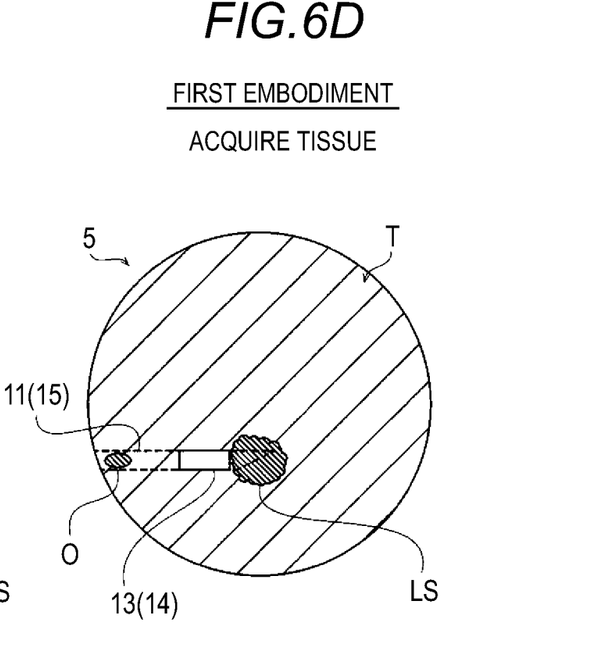
FIG. 6D is a schematic view of the nuclear medical diagnosis image when the tissue of the lesion area of the patient is acquired by the needle biopsy apparatus according to the first embodiment.

In Step S9, the operator acquires the tissue O in the lesion area LS of the patient T by manipulating the main body portion 12. The tomographic image is acquired at the time of acquiring the tissue O, and thus, as illustrated in FIG. 6C and FIG. 6D, it is possible to confirm that the tissue O moves through the needle 11.

Effects of First Embodiment

In the first embodiment, the following effects can be obtained.

In the first embodiment, as described above, the needle biopsy apparatus 10 for performing the needle biopsy with respect to the patient T while imaging at least a part of the needle 11, by using the nuclear medical diagnostic equipment 1, includes the hollow needle 11 for needling the patient T, and the main body portion 12 which retains the needle 11, and acquires the tissue O of the patient T through the needle 11, the needle 11 is configured of the solid not including the radioactive label, and includes the labelling portion 13 of which the radiation dose to be detected by the detection unit 2 of the nuclear medical diagnostic equipment 1 is less than that of the tissue O of the patient T ingesting the radioactive-labelled radiopharmaceutical dosed to the patient T, on the tip end side. Here, in the nuclear medical diagnostic equipment 1, in a case where the radiation dose to be detected by the detection unit 2 is small, in the image to be obtained, a portion of which the radiation dose is small, is drawn in whiter than the other portion, as the low-count region. Therefore, the labelling portion 13 of which the radiation dose to be detected by the detection unit 2 of the nuclear medical diagnostic equipment 1 is small, is included on the tip end side of the needle 11, and thus, it is possible to confirm the position of the biopsy needle 11 as an outline region in the nuclear medical diagnosis image 5 without disposing the radioactive-labelled labelling portion 13 in the needle 11. As a result thereof, it is possible to perform the needle biopsy by the needle 11 not including the radioactive-labelled labelling portion 13 (the RI radiation source), and thus, it is possible to make the management and the handling of the biopsy needle 11 under the nuclear medical diagnostic equipment 1 easy, and to reduce the dosage of the patient T and the operator.

In addition, in the first embodiment, as described above, the labelling portion 13 includes the solid radiation absorber 14. Here, in a case where the radiation absorber 14 is provided in the labelling portion 13, the radiation emitted from the body of the patient T is absorbed by the radiation absorber 14, and thus, it is possible to decrease the radiation dose to be detected by the detection unit 2. Therefore, in a case where the solid radiation absorber 14 is provided in the labelling portion 13, it is possible to reduce the radiation dose to be detected by the detection unit 2, and to confirm the tip end side (the labelling portion 13) of the needle 11 in the image.

In addition, in the first embodiment, as described above, the labelling portion 13 includes the radiation absorber 14 of which the absorption amount of the radiation emitted from the radioactive-labelled radiopharmaceutical dosed to the patient T is greater than that of the structure portion 15 of the needle 11 other than the labelling portion 13. Accordingly, it is possible to further increase the absorption amount of the radiation in the labelling portion 13 of the biopsy needle 11, than the structure portion 15 of the needle 11 other than the labelling portion 13. As a result thereof, in the image to be acquired by the nuclear medical diagnostic equipment 1, it is possible to easily identify the tip end side (the labelling portion 13) of the biopsy needle 11.

In addition, in first embodiment, as described above, the radiation absorber 14 is disposed separately from the needle 11, and is formed in the needle 11 into the shape of a cylinder along the inner circumferential surface of the needle 11. Accordingly, the radiation absorber 14 is formed into the shape of a cylinder, and thus, the tissue O is capable of penetrating through the radiation absorber 14 at the time of acquiring the tissue O. As a result thereof, it is possible to perform the needle biopsy in a state where the biopsy needle 11 is disposed on the tissue O to be acquired, without retreating the radiation absorber 14 from the needle 11 at the time of acquiring the tissue O, and thus, it is possible to shorten the procedure time.

In addition, in the first embodiment, as described above, the solid of the labelling portion 13 is the radiation absorber 14 of which the specific gravity is greater than or equal to 1 g/ml. Accordingly, in the labelling portion 13, it is possible to reduce the radiation dose to be detected by the detector.

In addition, in the first embodiment, as described above, Step S4 of needling the needle 11 of the needle biopsy apparatus 10 provided with the hollow needle 11, which is configured of the solid not including the radioactive label, and includes the labelling portion 13 of which the radiation dose to be detected by the detection unit 2 of the nuclear medical diagnostic equipment 1 is less than that of the tissue O of the patient T ingesting the radioactive-labelled radiopharmaceutical dosed to the patient T, towards the lesion area LS of the patient T, Step S5 of capturing an image of the region including the labelling portion 13 and the lesion area LS to which the radioactive-labelled radiopharmaceutical is dosed, by using the nuclear medical diagnostic equipment 1, and Step S6 to Step S9 of acquiring the tissue O from the lesion area LS by the needle 11, on the basis of the position of the labelling portion 13 and the lesion area LS in the image are included. Accordingly, in a case of performing the needle biopsy by the biopsy needle 11 not using the RI radiation source as the labelling portion 13, it is possible to confirm the position of the tip end side of the needle 11 by the labelling portion 13, and to perform the needling towards the lesion area LS. As a result thereof, it is possible to perform the needle biopsy by the needle 11 not including the radioactive-labelled labelling portion 13, and thus, it is possible to make the management and the handling of the biopsy needle 11 under the nuclear medical diagnostic equipment 1 easy, and to reduce the dosage of the patient T and the operator.

Second Embodiment

Next, a needle biopsy apparatus 30 according to a second embodiment of the invention will be described, with reference to FIG. 7. Unlike the first embodiment including the radiation absorber 14 which is disposed separately from the needle 11, and is formed in the needle 11 into the shape of a cylinder along the inner circumferential surface of needle 11, in the second embodiment, at least the tip end side of the needle 11 is formed of the radiation absorber 14. Furthermore, the same reference numerals are applied to the same configurations as those of the first embodiment described above, and the description thereof will be omitted.

Figure 7:
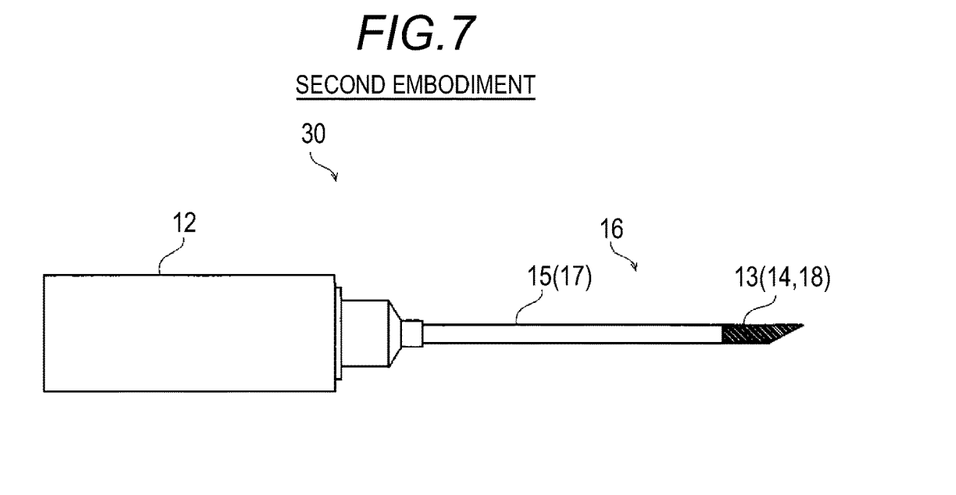
FIG. 7 is a schematic view when a needle biopsy apparatus according to a second embodiment is seen from a side surface.

As illustrated in FIG. 7, in the needle biopsy apparatus 30 of the second embodiment, at least a tip end side of a needle 16 is formed of the radiation absorber 14. Specifically, the needle 16 includes a first portion 17 on a root side, and a second portion 18 on the tip end side from the first portion 17. In addition, the labelling portion 13 of the needle 16 is integrally formed with the second portion 18 by the radiation absorber 14 of which the absorption amount of the radiation is greater than that of the first portion 17. That is, the second portion 18 is configured of a member having higher specific gravity than that of the first portion 17. For example, the first portion 17 is configured of stainless steel, and the second portion 18 is configured of lead, tungsten, or the like, of which the specific gravity is higher than that of stainless steel.

In addition, the second portion 18 may be configured to absorb the radiation more than the first portion 17. Therefore, in a case where the first portion 17 and the second portion 18 are configured of the same member, the absorption amount of the radiation in the second portion 18 may be greater than that in the first portion 17, by setting the thickness of the second portion 18 to be greater than the thickness of the first portion 17.

Furthermore, the other configuration of the second embodiment is identical to that of the first embodiment described above.

(Effects of Second Embodiment)

In the second embodiment, the following effects can be obtained.

In the second embodiment, as described above, at least the tip end side of the needle 16 is formed of the radiation absorber 14. Accordingly, it is possible to integrally provide the labelling portion 13 as a part of the needle 16. As a result thereof, it is possible to confirm the needle 16 in the image to be acquired by the nuclear medical diagnostic equipment 1, without disposing the radiation absorber 14 separate from the needle 16 in the needle 16, and thus, it is possible to suppress an increase in the number of components of the needle biopsy apparatus 30.

Furthermore, the other effect of the second embodiment is identical to that of the first embodiment described above.

Third Embodiment

Next, a needle biopsy apparatus 40 according to a third embodiment of the invention will be described, with reference to FIGS. 8A and 8B, and FIG. 9. Unlike the first embodiment including the radiation absorber 14 which is disposed separately from the needle 11, and is formed in the needle 11 into the shape of a cylinder along the inner circumferential surface of the needle 11, in the third embodiment, the radiation absorber 14 is disposed separately from the needle 19, and is disposed in a needle 19 to be detachable. The radiation absorber 14, for example, is fixed on a tip end side of the fixed needle 19 by being engaged with the needle 19. Furthermore, the same reference numerals are applied to the same configurations as those of the first embodiment described above, and the description thereof will be omitted.

Figure 8A:
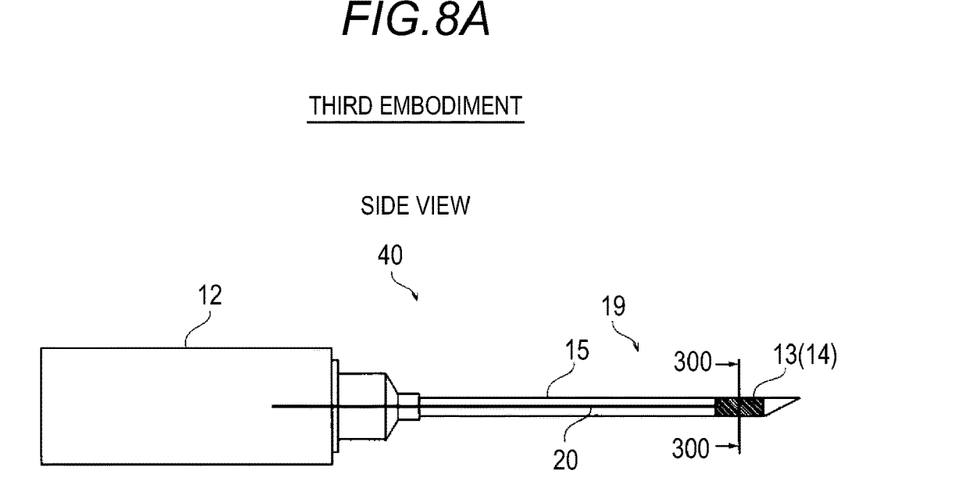
FIG. 8A is a schematic view when a needle biopsy apparatus according to a third embodiment is seen from a side surface.
Figure 8B:
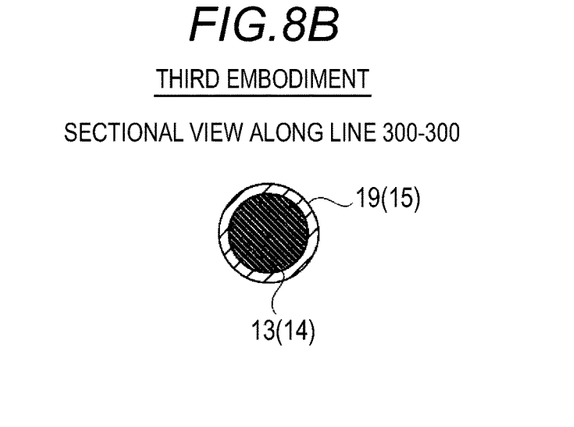
FIG. 8B is a sectional view along line 300-300 of FIG. 8A.
Figure 9:
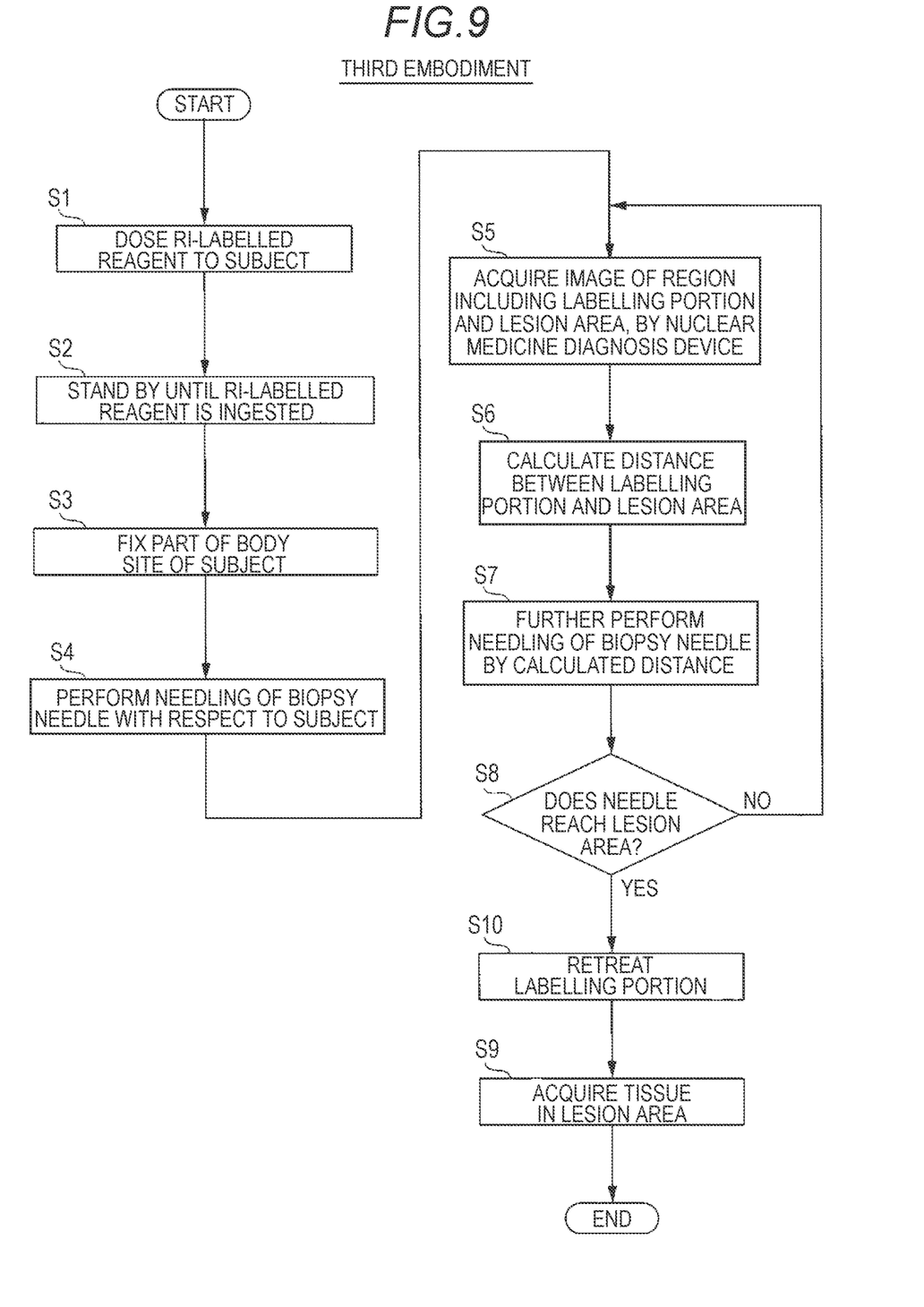
FIG. 9 is a flowchart for illustrating a needle biopsy method according to the third embodiment.

As illustrated in FIG. 8A, in the needle biopsy apparatus 40 of the third embodiment, the radiation absorber 14 is disposed separately from the needle 19, and is disposed in the needle 19 to be detachable. In addition, in the third embodiment, the needle biopsy apparatus 40 includes a wire 20 for retreating the radiation absorber 14 from the needle 19. In addition, unlike the first embodiment, in the third embodiment, as illustrated in FIG. 8B, the radiation absorber 14 is in a shape along an inner circumferential surface of the needle 19, in the needle 19. However, a cavity for allowing the tissue O to penetrate therethrough is not provided inside.

Therefore, in the third embodiment, Step S10 of retreating the radiation absorber 14 is further included. Specifically, as illustrated in FIG. 9, the needle 19 of the needle biopsy apparatus 40 reaches the lesion area LS of the patient T, according to Step S1 to Step S8. After that, in Step S10, the operator retreats the radiation absorber 14 from the needle 19 of the needle biopsy apparatus 40. After that, in Step S9, the operator acquires the tissue O of the lesion area LS by manipulating the main body portion 12.

Furthermore, the other configuration of the third embodiment is identical to that of the first embodiment described above.

Effects of Third Embodiment

In the third embodiment, the following effects can be obtained.

In the third embodiment, as described above, the radiation absorber 14 is disposed separately from the needle 19, and is disposed in the needle 19 to be detachable. Accordingly, the tissue O is acquired after the radiation absorber 14 is retreated from the needle 19, and thus, it is possible to increase a freedom degree of selecting the shape, the material, or the like of the radiation absorber 14 disposed in the needle 19.

Furthermore, the other configuration of the third embodiment is identical to that of the first embodiment described above.

(Modification Example)

Furthermore, the embodiments disclosed this time should be considered to be not limited in all respect, but as an example. The scope of the present invention is indicated by the scope of the claims but not by the description of the embodiments described above, and includes the equal meanings to the scope of the claims and all modifications (modification examples) within the scope.

For example, in the first embodiment to the third embodiment described above, an example has been described in which the operator needles the needle 11, but the invention is not limited thereto. For example, the needling of the needle 11 may be performed by using a device performing the needling of the needle 11 with respect to the patient T.

Figure 10A:
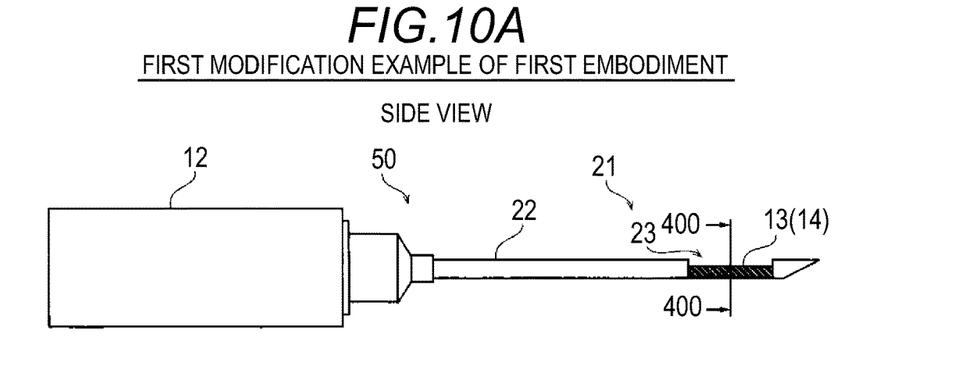
FIG. 10A is a schematic view when a needle biopsy apparatus according to a first modification example of the first embodiment is seen from a side surface.
Figure 10B:
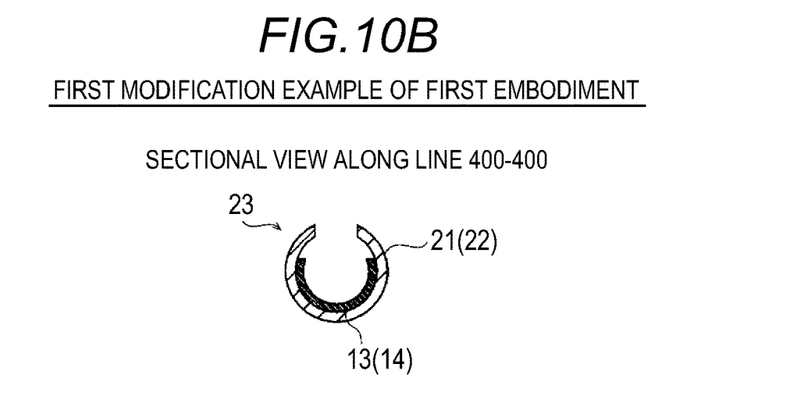
FIG. 10B is a sectional view along line 400-400 of FIG. 10A.
Figure 11:
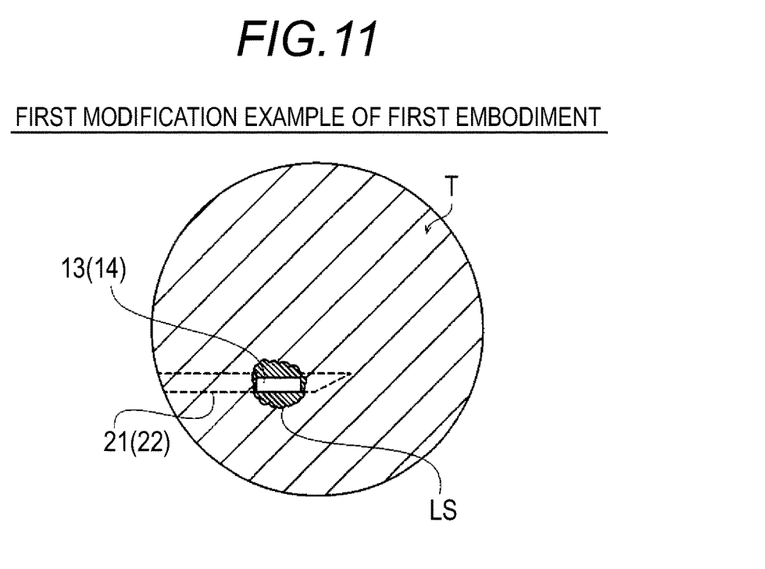
FIG. 11 is a schematic view for illustrating a position of a needle when a tissue is acquired by the needle biopsy apparatus according to the first modification example of the first embodiment.

In addition, in the first embodiment described above, an example of using the biopsy needle 11 acquiring the tissue O in the lesion area LS of the patient T from the tip end of the needle 11, has been described, but the invention is not limited thereto. For example, as with a needle biopsy apparatus 50 illustrated in FIGS. 10A and 10B, a needle 21 including the labelling portion 13 in a cutout portion 23 of the needle 21 provided with a cutout in a part of a structure portion 22 of a needle 21 on a tip end side, may be used. In this case, as illustrated in FIG. 11, the needling of the needle 21 may be performed until the labelling portion 13 reaches the inside of the lesion area LS, and after that, the tissue O may be acquired according to the manipulation of the operator. In examples illustrated in FIGS. 10A and 10B, for example, Mammotome (Registered Trademark) is performed. In this case, the main body portion 12 applies a suction pressure to the needle 21 according to the manipulation of the operator, and sucks the tissue O in the cutout portion 23 of the needle 21. After that, the main body portion 12 cuts the tissue O sucked in the cutout portion 23 of the needle 21 according to the manipulation of the operator, and acquires the tissue O.

Figure 12:
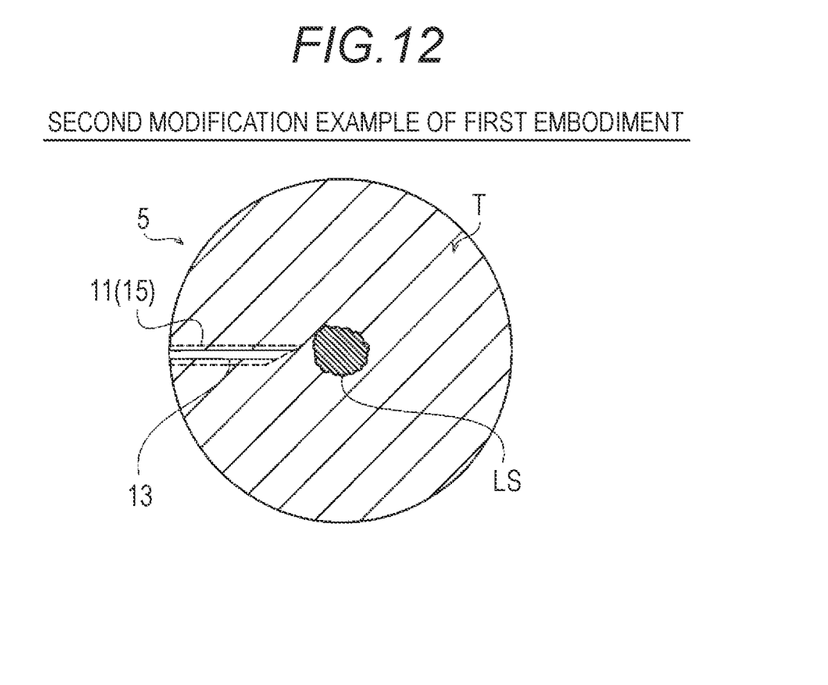
FIG. 12 is a schematic view when a needle biopsy apparatus according to a second modification example of the first embodiment is seen from a side surface.

In addition, in the first embodiment to the third embodiment described above, an example has been described in which the solid radiation absorber 14 is disposed as the labelling portion 13, but the invention is not limited thereto. For example, the needle 11 may include the labelling portion 13 configured of gas not including a radioactive label or a liquid not including a radioactive label, such as a normal saline solution. That is, the labelling portion 13 may be configured of air as gas, or may be configured of a liquid. In a case where the labelling portion 13 contains the air, the labelling portion 13 does not include the RI radiation source, and thus, the radiation dose emitted from the labelling portion 13 is less than the radiation dose emitted from the other portion, and therefore, it is possible to decrease the radiation dose to be detected by the detection unit 2. Therefore, as illustrated in FIG. 12, even in a case where the labelling portion 13 contains the air, it is possible to reduce the radiation dose to be detected by the detection unit 2, and to confirm the needle 11 (the labelling portion 13) in the nuclear medical diagnosis image 5. Furthermore, in a case where the labelling portion 13 is configured of the air, it is preferable that the needle 11 is formed to be large (thick) in order to be easily recognized in the nuclear medical diagnosis image 5.

Figure 13:
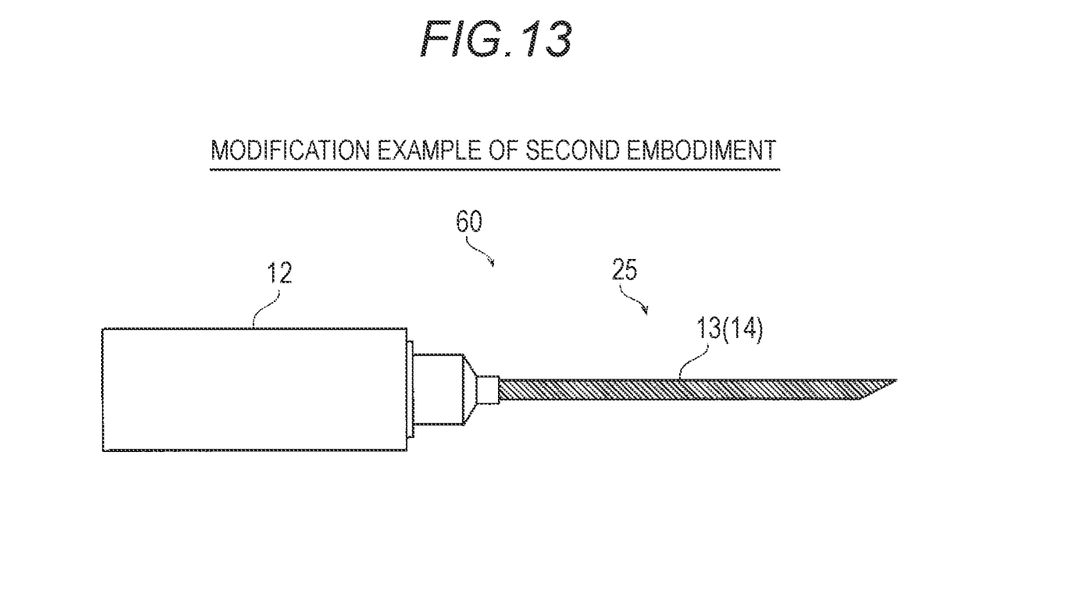
FIG. 13 is a schematic view when a needle biopsy apparatus according to a modification example of the second embodiment is seen from a side surface.

In addition, in the second embodiment described above, an example has been described in which the labelling portion 13 is integrally formed in the tip end portion of the needle 16, but the invention is not limited thereto. For example, as with a needle biopsy apparatus 60 illustrated in FIG. 13, a needle 24 may be configured of the radiation absorber 14, and thus, the entire needle 24 may function as the labelling portion 13.

In addition, in the first embodiment described above, a step of confirming that whether or not the needle 11 reaches the lesion area LS is provided after the needling of the needle 11 with respect to the patient T, but the invention is not limited thereto. For example, in a case where the needling of the needle 11 is further performed by a predetermined distance than the calculated distance D, the step of confirming whether or not the needle 11 reaches the lesion area LS may be omitted.

In addition, in the first embodiment to the third embodiment described above, an example has been described in which the tomographic image of the region including the labelling portion 13 and the lesion area LS is generated, in order to calculate the distance D between the labelling portion 13 and the lesion area LS, but the invention is not limited thereto. For example, a 3D image other than the tomographic image may be generated, and thus, the distance D between the labelling portion 13 and the lesion area LS may be calculated. Any image may be generated insofar as the distance D between the labelling portion 13 and the lesion area LS can be calculated.

The invention claimed is:

1. A needle biopsy apparatus for performing a needle biopsy with respect to a patient while imaging at least a part of a needle, by using a nuclear medical diagnostic equipment, the needle biopsy apparatus comprising:
   a hollow needle for needling the patient; and
   a main body portion which retains the needle, and acquires a tissue of the patient through the needle,
   wherein the needle is configured of gas not including a radioactive label, a liquid not including a radioactive label, or a solid not including a radioactive label, and includes a labelling portion of which a radiation dose to be detected by a detection unit of the nuclear medical diagnostic equipment is less than that of the tissue of the patient ingesting a radioactive-labelled radiopharmaceutical dosed to the patient, on a tip end side, and
   wherein the labeling portion is a part of the needle, and the labelling portion absorbs a radiation emitted from the radioactive-labelled radiopharmaceutical dosed to the patient, more than a structure portion of the needle other than the labelling portion.

2. The needle biopsy apparatus according to claim 1, wherein the labelling portion includes an air or liquid radiation absorber, or a solid radiation absorber.

3. The needle biopsy apparatus according to claim 1, wherein the labelling portion includes a radiation absorber which absorbs a radiation emitted from the radioactive-labelled radiopharmaceutical dosed to the patient, more than a structure portion of the needle other than the labelling portion.

4. The needle biopsy apparatus according to claim 3, wherein the radiation absorber is disposed separately from the needle, and is formed in the needle into the shape of a cylinder along an inner circumferential surface of the needle.

5. The needle biopsy apparatus according to claim 3, wherein in the needle, at least the tip end side is formed of the radiation absorber.

6. The needle biopsy apparatus according to claim 3, wherein the radiation absorber is disposed separately from the needle, and is disposed in the needle to be detachable.

7. The needle biopsy apparatus according to claim 1, wherein the liquid or the solid of the labelling portion is a radiation absorber having specific gravity of greater than or equal to 1 g/ml.

8. A needle biopsy method, comprising:
   a step of needling a needle of a needle biopsy apparatus provided with a hollow needle, which is configured of gas not including a radioactive label, a liquid not including a radioactive label, or a solid not including a radioactive label, and includes a labelling portion of which a radiation dose to be detected by a detection unit of a nuclear medical diagnostic equipment is less than that of a tissue of a patient ingesting a radioactive-labelled radiopharmaceutical dosed to the patient, towards a lesion area of the patient;
   a step of capturing an image of a region including the labelling portion and the lesion area to which the radioactive-labelled radiopharmaceutical is dosed, by using the nuclear medical diagnostic equipment; and
   a step of acquiring the tissue from the lesion area by the needle, on the basis of a position of the labelling portion and the lesion area in the image, wherein the labeling portion is a part of the needle, and the labelling portion absorbs a radiation emitted from the radioactive-labelled radiopharmaceutical dosed to the patient, more than a structure portion of the needle other than the labelling portion.

9. A needle biopsy system, comprising:
   a needle biopsy apparatus; and
   a nuclear medical diagnostic equipment,
   wherein the needle biopsy apparatus for performing a needle biopsy with respect to a patient while imaging at least a part of a needle, by using the nuclear medical diagnostic equipment, includes,
   a hollow needle for needling the patient, and
   a main body portion which retains the needle, and acquires a tissue of the patient through the needle,
   the needle is configured of gas not including a radioactive label, a liquid not including a radioactive label, or a solid not including a radioactive label, and includes a labelling portion of which a radiation dose to be detected by a detection unit of the nuclear medical diagnostic equipment is less than that of the tissue of the patient ingesting a radioactive-labelled radiopharmaceutical dosed to the patient, on a tip end side, and
   the nuclear medical diagnostic equipment acquires an image of a region including the labelling portion and a lesion area of the patient, wherein the labeling portion is a part of the needle, and the labelling portion absorbs a radiation emitted from the radioactive-labelled radiopharmaceutical dosed to the patient, more than a structure portion of the needle other than the labelling portion.

* * * * *